(12) United States Patent
Sharma et al.

(10) Patent No.: US 8,044,243 B2
(45) Date of Patent: Oct. 25, 2011

(54) COMPOUNDS FOR THE TREATMENT OF METABOLIC DISORDERS

(75) Inventors: Shalini Sharma, Gaithersburg, MD (US); Reid W. von Borstel, Potomac, MD (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 690 days.

(21) Appl. No.: 12/279,247

(22) PCT Filed: Feb. 9, 2007

(86) PCT No.: PCT/US2007/061908
§ 371 (c)(1),
(2), (4) Date: Aug. 13, 2008

(87) PCT Pub. No.: WO2007/095462
PCT Pub. Date: Aug. 23, 2007

(65) Prior Publication Data
US 2009/0176889 A1    Jul. 9, 2009

Related U.S. Application Data

(60) Provisional application No. 60/772,687, filed on Feb. 13, 2006.

(51) Int. Cl.
| | |
|---|---|
| *C07C 211/00* | (2006.01) |
| *C07C 21/18* | (2006.01) |
| *C07C 17/00* | (2006.01) |
| *C07C 19/08* | (2006.01) |
| *C07C 22/00* | (2006.01) |
| *C07C 25/13* | (2006.01) |
| *C07C 19/00* | (2006.01) |
| *C07C 21/00* | (2006.01) |
| *C07C 23/00* | (2006.01) |
| *C07C 25/00* | (2006.01) |

(52) U.S. Cl. ......... 564/337; 570/126; 570/127; 570/101
(58) Field of Classification Search ................... None
See application file for complete search history.

(56) References Cited

U.S. PATENT DOCUMENTS

| | | |
|---|---|---|
| 6,232,322 B1 | 5/2001 | Malamas et al. |
| 6,307,080 B1 | 10/2001 | Pischel et al. |
| 6,858,602 B2 | 2/2005 | Sharma et al. |
| 6,916,848 B2 | 7/2005 | Sharma |
| 6,924,314 B2 | 8/2005 | Sharma et al. |
| 6,946,491 B2 | 9/2005 | Sharma et al. |
| 7,012,071 B2 | 3/2006 | Sharma et al. |
| 7,041,659 B2 | 5/2006 | Sharma |
| 7,045,541 B2 | 5/2006 | Sharma |
| 7,101,910 B2 | 9/2006 | Sharma |
| 7,329,782 B2 | 2/2008 | Sharma et al. |
| 7,361,686 B2 | 4/2008 | Hodge et al. |
| 7,442,796 B2 | 10/2008 | Sharma et al. |
| 2002/0064847 A1 | 5/2002 | Yamamoto et al. |
| 2005/0090555 A1 | 4/2005 | Sharma et al. |
| 2006/0014784 A1 | 1/2006 | Hodge et al. |
| 2006/0035970 A1 | 2/2006 | Hodge et al. |
| 2006/0247309 A1 | 11/2006 | Hodge et al. |
| 2007/0105958 A1 | 5/2007 | Sharma et al. |
| 2007/0249696 A1 | 10/2007 | Sharma et al. |
| 2007/0249719 A1 | 10/2007 | Sharma et al. |
| 2007/0265322 A1 | 11/2007 | Sharma et al. |
| 2007/0282003 A1 | 12/2007 | Sharma et al. |
| 2008/0015209 A1 | 1/2008 | Sharma et al. |
| 2008/0015254 A1 | 1/2008 | Hodge et al. |
| 2008/0021109 A1 | 1/2008 | Sharma et al. |
| 2008/0027229 A1 | 1/2008 | Hodge et al. |

FOREIGN PATENT DOCUMENTS

| | | | |
|---|---|---|---|
| GB | 2249309 | * | 5/1992 |
| JP | 07089898 | * | 4/1995 |
| WO | 02/100341 A2 | | 12/2002 |
| WO | 2004/073611 A2 | | 9/2004 |
| WO | 2004/091486 A2 | | 10/2004 |

OTHER PUBLICATIONS

Younis, et al., "The prevention of type 2 diabetes mellitus: recent advances", QJ Med., vol. 97, pp. 451-455, 2004.
Goff, et al., "Prevention of Cardiovascular Disease in Persons with type 2 diabetes Mellitus: Current Knowledge and Rational for the Action to Control Cardiovascular Risk in Diabetes (ACCORD) Trial", AM J Cardiol., 99(12A): S4-S20, 2007. (Abstract).
Knowler, et al., "Perspectives in Diabetes: Preventing Non-Insulin-Dependent Diabetes", Diabetes, vol. 44, pp. 483-488, 1995.
Pending (as of Mar. 24, 2008) claims from U.S. Appl. No. 11/772,515.
Pending (as of Mar. 24, 2008) claims from U.S. Appl. No. 11/772,520.
Pending (as of Mar. 24, 2008) claims from U.S. Appl. No. 11/772,560.

(Continued)

*Primary Examiner* — Daniel Sullivan
*Assistant Examiner* — Clinton Brooks
(74) *Attorney, Agent, or Firm* — Lewis J. Kreisler

(57) ABSTRACT

Agents useful for the treatment of various metabolic disorders, such as insulin resistance syndrome, diabetes, polycystic ovary syndrome, hyperlipidemia, fatty liver disease, cachexia, obesity, atherosclerosis and arteriosclerosis are disclosed. Formula (I) wherein n is 1 or 2; q is 0 or 1; t is 0 or 1; $R^1$ is alkyl having from 1 to 3 carbon atoms; $R^2$ is hydrogen, halo, alkyl having from 1 to 3 carbon atoms, or alkoxy having from 1 to 3 carbon atoms; A is unsubstituted or substituted phenyl; or cycloalkyl; or a 5 or 6 membered heteroaromatic ring. Alternatively, the agent can be a pharmaceutically acceptable salt of the compound of Formula I.

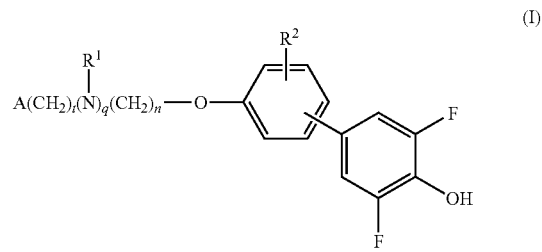

10 Claims, No Drawings

OTHER PUBLICATIONS

Pending (as of Sep. 25, 2008) claims from U.S. Appl. No. 12/294,530.
Pending (as of Jul. 14, 2008) claims from U.S. Appl. No. 12/160,857.
Pending (as of Jul. 28, 2008) claims from U.S. Appl. No. 12/162,397.
Pending (as of May 7, 2008) claims from U.S. Appl. No. 12/092,932.
Pending (as of Aug. 18, 2008) claims from U.S. Appl. No. 12/160,808.
Pending (as of Jul. 14, 2008) claims from U.S. Appl. No. 12/160,858.
Pending (as of Jul. 14, 2008) claims from U.S. Appl. No. 12/160,854.

* cited by examiner

COMPOUNDS FOR THE TREATMENT OF METABOLIC DISORDERS

BACKGROUND OF THE INVENTION

Diabetes mellitus is a major cause of morbidity and mortality. Chronically elevated blood glucose leads to debilitating complications: nephropathy, often necessitating dialysis or renal transplant; peripheral neuropathy; retinopathy leading to blindness; ulceration of the legs and feet, leading to amputation; fatty liver disease, sometimes progressing to cirrhosis; and vulnerability to coronary artery disease and myocardial infarction.

There are two primary types of diabetes. Type I, or insulin-dependent diabetes mellitus (IDDM) is due to autoimmune destruction of insulin-producing beta cells in the pancreatic islets. The onset of this disease is usually in childhood or adolescence. Treatment consists primarily of multiple daily injections of insulin, combined with frequent testing of blood glucose levels to guide adjustment of insulin doses, because excess insulin can cause hypoglycemia and consequent impairment of brain and other functions.

Type II, or noninsulin-dependent diabetes mellitus (NIDDM) typically develops in adulthood. NIDDM is associated with resistance of glucose-utilizing tissues like adipose tissue, muscle, and liver, to the actions of insulin. Initially, the pancreatic islet beta cells compensate by secreting excess insulin. Eventual islet failure results in decompensation and chronic hyperglycemia. Conversely, moderate islet insufficiency can precede or coincide with peripheral insulin resistance. There are several classes of drugs that are useful for treatment of NIDDM: 1) insulin releasers, which directly stimulate insulin release, carrying the risk of hypoglycemia; 2) prandial insulin releasers, which potentiate glucose-induced insulin secretion, and must be taken before each meal; 3) biguanides, including metformin, which attenuate hepatic gluconeogenesis (which is paradoxically elevated in diabetes); 4) insulin sensitizers, for example the thiazolidinedione derivatives rosiglitazone and pioglitazone, which improve peripheral responsiveness to insulin, but which have side effects like weight gain, edema, and occasional liver toxicity; 5) insulin injections, which are often necessary in the later stages of NIDDM when the islets have failed under chronic hyperstimulation.

Insulin resistance can also occur without marked hyperglycemia, and is generally associated with atherosclerosis, obesity, hyperlipidemia, and essential hypertension. This cluster of abnormalities constitutes the "metabolic syndrome" or "insulin resistance syndrome". Insulin resistance is also associated with fatty liver, which can progress to chronic inflammation (NASH; "nonalcoholic steatohepatitis"), fibrosis, and cirrhosis. Cumulatively, insulin resistance syndromes, including but not limited to diabetes, underlie many of the major causes of morbidity and death of people over age 40.

Despite the existence of such drugs, diabetes remains a major and growing public health problem. Late stage complications of diabetes consume a large proportion of national health care resources. There is a need for new orally active therapeutic agents which effectively address the primary defects of insulin resistance and islet failure with fewer or milder side effects than existing drugs.

Currently there are no safe and effective treatments for fatty liver disease. Therefore such a treatment would be of value in treating this condition.

SUMMARY OF THE INVENTION

This invention provides a biologically active agent as described below. This invention provides the use of the biologically active agent described below in the manufacture of a medicament for the treatment of insulin resistance syndrome, diabetes, cachexia, hyperlipidemia, fatty liver disease, obesity, atherosclerosis or arteriosclerosis. This invention provides methods of treating a mammalian subject with insulin resistance syndrome, diabetes, cachexia, hyperlipidemia, fatty liver disease, obesity, atherosclerosis or arteriosclerosis comprising administering to the subject an effective amount of the biologically active agent described below. This invention provides a pharmaceutical composition comprising the biologically active agent described below and a pharmaceutically acceptable carrier.

The biologically active agent in accordance with this invention is a compound of Formula I:

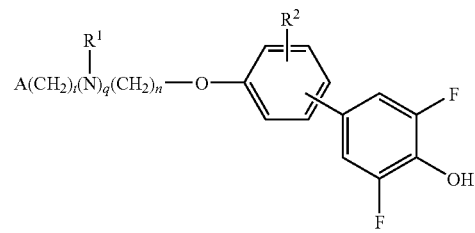

wherein n is 1 or 2; q is 0 or 1; t is 0 or 1; $R^1$ is alkyl having from 1 to 3 carbon atoms; $R^2$ is hydrogen, halo, alkyl having from 1 to 3 carbon atoms, or alkoxy having from 1 to 3 carbon atoms; A is phenyl, unsubstituted or substituted by 1 or 2 groups selected from: halo, alkyl having 1 or 2 carbon atoms, perfluoromethyl, hydroxy, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon. Alternatively, the biologically active agent can be a pharmaceutically acceptable salt of the compound of Formula I.

It is believed that the biologically active agents of this invention will have activity in one or more of the biological activity assays described below, which are established animal models of human diabetes and insulin resistance syndrome. Therefore such agents would be useful in the treatment of diabetes and insulin resistance syndrome.

DETAILED DESCRIPTION OF THE INVENTION

Definitions

As used herein the term "alkyl" means a linear or branched-chain alkyl group. An alkyl group identified as having a certain number of carbon atoms means any alkyl group having the specified number of carbons. For example, an alkyl having three carbon atoms can be propyl or isopropyl; and alkyl having four carbon atoms can be n-butyl, 1-methylpropyl, 2-methylpropyl or t-butyl.

As used herein the term "halo" refers to one or more of fluoro, chloro, bromo, and iodo.

As used herein the term "perfluoro" as in perfluoromethyl or perfluoromethoxy, means that the group in question has fluorine atoms in place of all of the hydrogen atoms.

As used herein "Ac" refers to the group $CH_3C(O)—$.

Certain chemical compounds are referred to herein by their chemical name or by the two-letter code shown below. Compound DG is included within the scope of Formula I shown above.

DG  2,6-Difluoro-4-(3-(2,6-dimethylbenzyloxy)phenyl) phenol.

As used herein the transitional term "comprising" is open-ended. A claim utilizing this term can contain elements in addition to those recited in such claim.

COMPOUNDS OF THE INVENTION

In an embodiment of the agent, use, method or pharmaceutical composition described in the Summary above, n is 1; q is 0; t is 0; $R^2$ is hydrogen; and A is phenyl, unsubstituted or substituted by 1 or 2 groups selected from: halo, hydroxy, alkyl having 1 or 2 carbon atoms, perfluoromethyl, alkoxy having 1 or 2 carbon atoms, and perfluoromethoxy. In an embodiment of this invention "A" is 2,6-dimethylphenyl. Examples of such compounds include Compound DG.

In an embodiment of the biologically active agent of this invention, the agent is in substantially (at least 98%) pure form.

Reaction Schemes

The biologically active agents of the present invention can be made in accordance with the following reaction schemes.

The compound of formula I where q is 0 or 1, t is 0 or 1, and n is 1 or 2, $R^1$ is alkyl having from 1 to 3 carbon atoms, and $R^2$ is hydrogen, halo, alkoxy having from 1 to 3 carbon atoms, i.e. compounds of formula:

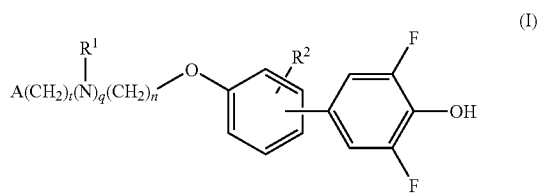

(I)

wherein A is described as above, can be prepared via reaction of scheme 1.

In the reaction of scheme 1, A, t, n, q, $R^1$, and $R^2$ are as above. P is a hydrolyzable ester-protecting group. X is bromide or iodide.

The compound of formula IV can be synthesized by Suzuki Coupling or using a Fu protocol by cross-coupling reaction of the compound of formula II with boronic ester of the compound of formula III via reaction of step (a). The reaction is catalyzed by palladium for example tris(dibenzylideneacetone)dipalladium (0), tetrakis (triphenylphosphine)palladium (0), bis(triphenylphosphine)palladium (II) chloride and the like. The reaction is carried out in the presence of a base for example cesium carbonate, potassium carbonate, sodium carbonate, cesium fluoride, potassium fluoride and the like. Generally the reaction is carried out in solvents for example tetrahydrofuran, 1,2-dimethoxyethane, benzene and the like. Generally the reaction is carried out at temperatures of from 0° C. to reflux. Any of the conditions conventional in Suzuki couplings can be utilized to carry out the reaction of step (a). The product can be isolated and purified by techniques such as extraction, evaporation, chromatography, and recrystallization.

The compound of formula IV can be converted to the compound of formula I via reaction of step (b) by deprotecting the protecting group utilizing suitable deprotecting reagents such as those described in Protective Groups in Organic Synthesis by T. Greene.

If A is phenyl substituted by 1 or 2 groups of hydroxyl, it is generally preferred to protect the hydroxyl group with the suitable protecting group which protects the hydroxyl group throughout the reaction. The suitable protecting group can be described in the Protective Groups in Organic Synthesis by T. Greene.

The protecting group can be deprotected utilizing suitable deprotecting reagents such as those described in Protective Groups in Organic Synthesis by T. Greene.

Reaction Scheme 1

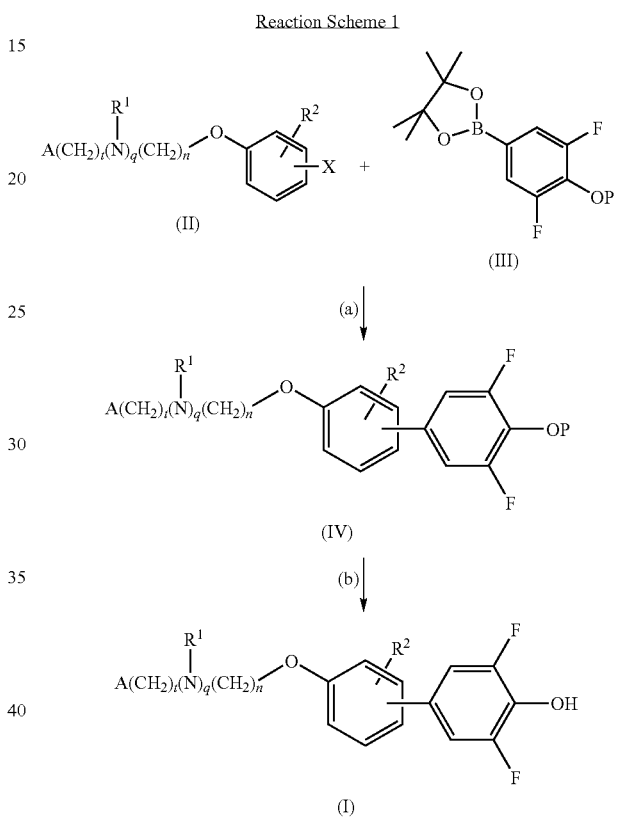

The compound of formula II where q is 0 or 1, t is 0 or 1, and n is 1 or 2, $R^1$ is alkyl having from 1 to 3 carbon atoms, $R^2$ is hydrogen, halo, alkoxy having from 1 to 3 carbon atoms or alkyl having from 1 to 3 carbon atoms and X is bromide or iodide, i.e. compounds of formula:

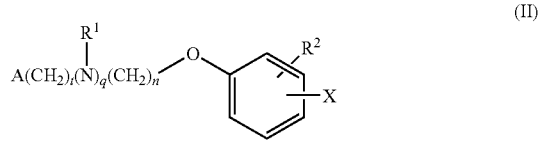

(II)

wherein A is described as above, can be prepared via reaction of scheme 2.

In the reaction of scheme 2, A, t, n, q, $R^1$, and $R^2$ are as above. X is bromide or iodide and Y is a leaving group or halide. Y' is chloro or bromo.

The compound of formula V can be converted to the compound of formula IX via reaction of step (c) using Mitsunobu condensation of V with VI using triphenylphosphine and diethyl azodicarboxylate or diisopropyl azodicarboxylate. The reaction is carried out in a suitable solvent for example tetrahydrofuran. Any of the conditions conventionally used in Mitsunobu reactions can be utilized to carry out the reaction of step (c).

The compound of formula IX can also be prepared by etherifying or alkylating the compound of formula V with the compound of formula VII or the compound of formula VIII as in reaction of step (c). In the compound of formula VII, Y, include but are not limited to mesyloxy, tosyloxy, chloro, bromo, iodo, and the like. Any conventional method of etherifying of a hydroxyl group by reaction with a leaving group or halide can be utilized to carry out the reaction of step (c). The product can be isolated and purified by techniques such as extraction, evaporation, chromatography, and recrystallization.

The compound of formula IX is the compound of formula II where q is 0 or 1.

If A is phenyl substituted by 1 or 2 groups of hydroxyl, it is generally preferred to protect the hydroxyl group with the suitable protecting group which protects the hydroxyl group throughout the reaction. The suitable protecting group can be described in the Protective Groups in Organic Synthesis by T. Greene.

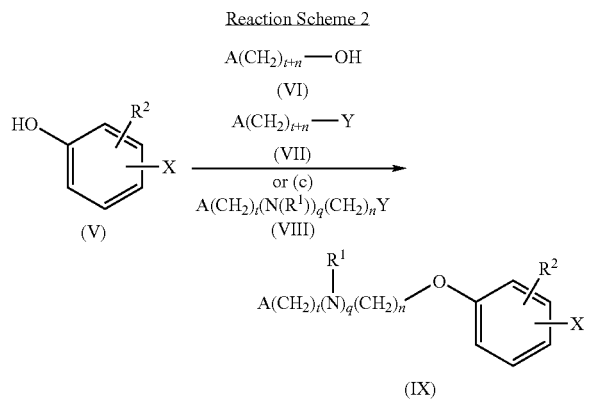

The compound of formula III,

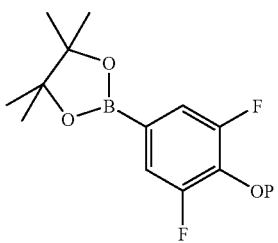

wherein P is a hydrolyzable ester protecting group, can be prepared via reaction of scheme 3. In the reaction of scheme 3, P is as above.

In the compound of formula X, the phenol group can be protected via reaction of step (d) by hydrolyzable protecting group such as lower alkanoyl group. The suitable protecting group can be described in the Protective Groups in Organic Synthesis by T. Greene.

The compound of formula XI can be converted to the compound of formula XII via reaction of step (e) by reducing nitro group to an amino group. Any conventional reducing agent for example Zn, Sn, Fe and acid can be utilized to carry out the reaction of step (e). The compound of formula XI can also be reduced to the compound of formula XII via hydrogenation. Among the conventional methods of hydrogenation are for example with hydrogen gas in the presence of 10% Pd/C in ethanol, heterogeneous catalytic transfer hydrogenation using either 1,4-cyclohexadiene or cyclohexene in ethanol and the like. Generally the reaction is carried out at temperatures of from 0° C. to reflux. Any of the conditions conventional in such reduction reactions can be utilized to carry out the reaction of step (e).

The compound of formula XII can be converted to the aryl bromide of the formula XIII via reaction of step (f) by Sandmeyer reaction by reacting the compound of formula XII with sodium nitrite in 48% HBr and anhydrous copper bromide. Generally the reaction is carried out at temperatures of from 0° C. to reflux. Any of the conditions conventionally used in Sandmeyer reactions can be utilized to carry out the reaction of step (f).

The compound of formula XIII can be converted to the compound of formula III via reaction of step (g) by cross-coupling reaction of the compound of formula XIII with bis (pinacolato) diboron using catalyst for example [1,1bis (diphenylphosphino)ferrocene]dichloropalladim (II), bis (triphenylphosphine)palladium (II) chloride and the like. Generally the reaction is carried out utilizing a suitable base for example potassium acetate, triethylamine and the like. The reaction is carried out in conventional solvents such as dioxane, toluene, dimethyl sulphoxide and the like. Generally the reaction is carried out at temperatures of from 0° C. to reflux. Any of the conditions conventionally used in Miyaura borylation reaction can be utilized to carry out the reaction of step (g). The product can be isolated and purified by techniques such as extraction, evaporation, chromatography, and recrystallization.

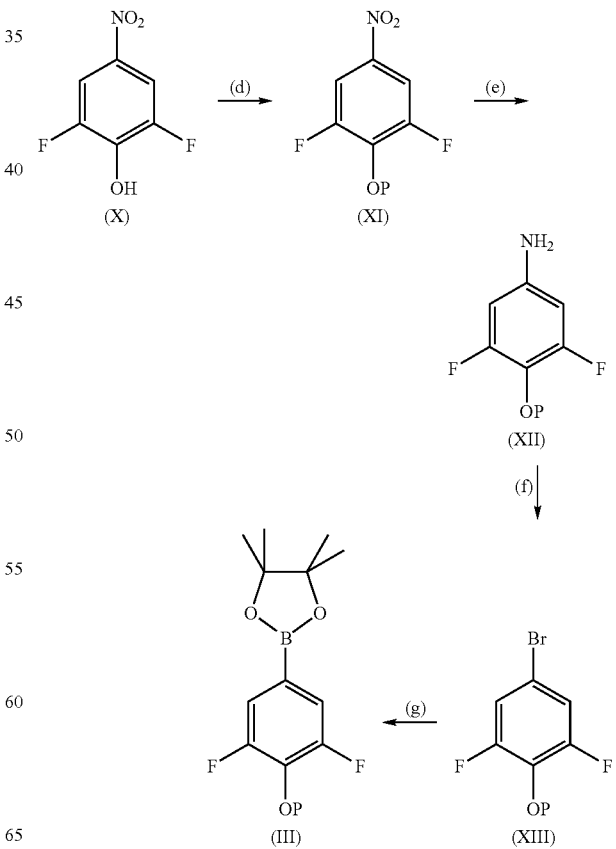

The compound of formula VI, where t is 0 or 1, n is 1 or 2, i.e. compounds of formula:

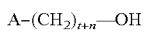

and the compound of formula VII, where t is 0 or 1, n is 1 or 2, i.e. compounds of formula:

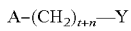

can be prepared via reaction of scheme 4. In the reaction of scheme 4, A is described as above. Y is a leaving group.

The compound of formula XIV can be reduced to the compound of formula XV via reaction of step (h). The reaction is carried out utilizing a conventional reducing agent for example alkali metal hydride such as lithium aluminum hydride. The reaction is carried out in a suitable solvent, such as tetrahydrofuran. Any of the conditions conventional in such reduction reactions can be utilized to carry out the reaction of step (h). The compound of formula XV is the compound of formula VI where t is 0 and n is 1.

The compound of formula XV can be converted to the compound of formula XVI by displacing hydroxyl group with a halogen group preferred halogen being bromo or chloro. Appropriate halogenating reagents include but are not limited to thionyl chloride, bromine, phosphorous tribromide, carbon tetrabromide and the like. Any conditions conventional in such halogenation reactions can be utilized to carry out the reaction of step (i). The compound of formula XVI is the compound of formula VII where t is 0 and n is 1.

The compound of formula XVI can be converted to the compound of formula XVII by reacting XVI with an alkali metal cyanide for example sodium or potassium cyanide. The reaction is carried out in a suitable solvent, such as ethanol or dimethyl sulfoxide. Any of the conditions conventionally used in the preparation of nitrile can be utilized to carry out the reaction of step (j).

The compound of formula XVII can be converted to compound of formula XVIII via reaction step (k) by acid or base hydrolysis. In carrying out this reaction it is generally preferred to utilize basic hydrolysis, for example aqueous sodium hydroxide. Any of the conditions conventionally used in hydrolysis of nitrile can be utilized to carry out the reaction of step (k).

The compound of formula XVIII can be reduced to give the compound of formula XIX via reaction of step (l). This reaction can be carried out in the same manner as described hereinbefore in the reaction of step (h). The compound of formula XIX is the compound of formula VI where t is 1 and n is 1.

The compound of formula XIX can be converted to the compound of formula XX via reaction of step (m) in the same manner as described hereinbefore in connection with the reaction of step (i). The compound of formula XX is the compound of formula VII where t is 1 and n is 1.

The compound of formula XVI can be reacted with diethyl malonate utilizing a suitable base for example sodium hydride to give the compound of formula XXI. The reaction is carried out in suitable solvents, such as dimethylformamide, tetrahydrofuran and the like. Any of the conditions conventional in such alkylation reactions can be utilized to carry out the reaction of step (n).

The compound of formula XXI can be hydrolyzed and decarboxylated utilizing sodium hydroxide in suitable solvent, such as ethanol-water to give the compound of formula XXII. Any of the conditions conventional in such reactions can be utilized to carry out the reaction of step (o).

The compound of formula XXII can be converted to the compound of formula XXIII via reaction of step (p) in the same manner as described hereinbefore in connection with the reaction of step (h). The compound of formula XXIII is the compound of formula VII where t is 1 and n is 2.

The compound of formula XXIII can be converted to the compound of formula XXIV via reaction of step (q) in the same manner as described hereinbefore in connection with the reaction of step (i). The compound of formula XXIV is the compound of formula VII where t is 1 and n is 2. The products can be isolated and purified by techniques such as extraction, evaporation, chromatography, and recrystallization.

If A is phenyl substituted by 1 or 2 groups of hydroxyl, it is generally preferred to protect the hydroxyl group of the compound of formula XIV. The suitable protecting group can be described in the Protective Groups in Organic Synthesis by T. Greene.

Reaction Scheme 4

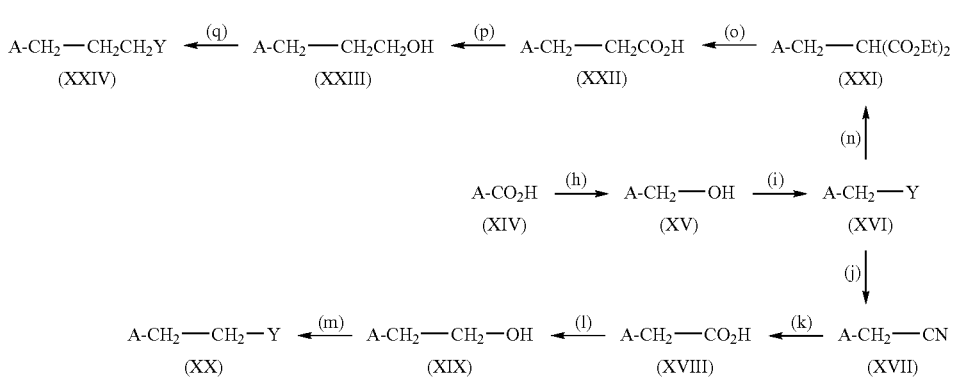

The compound of formula VIII, where t is 0 or 1, n is 1 or 2, q is 1 and Y is chloro or bromo, i.e. compounds of formula:

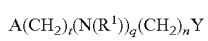

can be prepared via reaction of scheme 5. In the reaction of scheme 5, A and Y are described as above.

The compound of formula XXV can be mesylated to furnish the compound of formula XXVI via reaction of step (r). Any conventional conditions to carry out the mesylation reaction of a hydroxyl group can be utilized to carry out the reaction of step (r). The compound of formula XXVI can be heated with the compound of formula XXVII to produce the compound of formula XXVIII. Any of the conditions conventional to produce amino alcohol can be utilized to carry out the reaction of step (s).

In the compound of formula XXVIII, alcohol can be displaced by chloro or bromo by treating the compound of formula XXVIII with thionyl chloride, oxalyl chloride, bromine, phosphorus tribromide, carbon tetrabromide and the like to produce the compound of formula VIII. Any conventional method to displace alcohol with chloro or bromo can be utilized to carry out the reaction of step (t).

If A is phenyl substituted by 1 or 2 groups of hydroxyl, it is generally preferred to protect the hydroxyl group of the compound of formula XXV. The suitable protecting group can be described in the Protective Groups in Organic Synthesis by T. Greene.

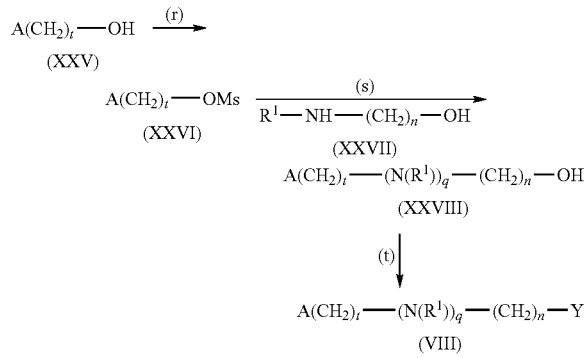

The compound of formula V where $R^2$ is hydrogen, halo, alkoxy having from 1 to 3 carbon atoms or alkyl having from 1 to 3 carbon atoms and X is bromide or iodide, i.e. compounds of formula:

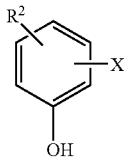

can be prepared via reaction of scheme 6.

In the reaction of scheme 6, P is a protective group.

In the compound of formula XXIX, hydroxyl group can be protected by means of forming hydrolyzable protecting group, which protects the hydroxyl group throughout the reaction. The suitable protecting group can be described in the Protective Groups in Organic Synthesis by T. Greene. Any conditions conventional in protecting the hydroxyl group can be utilized to carry out the reaction of step (u).

The compound of formula XXX can be converted to the compound of formula XXXI via reaction of step (v) by reducing nitro group to an amino group. Any conventional reducing agent for example Zn, Sn, Fe and acid can be utilized to carry out the reaction of step (v). The compound of formula XXX can also be reduced to the compound of formula XXXI via hydrogenation. Among the conventional methods of hydrogenation are for example with hydrogen gas in the presence of 10% Pd/C in ethanol, heterogeneous catalytic transfer hydrogenation using either 1,4-cyclohexadiene or cyclohexene in ethanol and the like. Generally the reaction is carried out at temperatures of from 0° C. to reflux. Any of the conditions conventional in such reduction reactions can be utilized to carry out the reaction of step (v).

The compound of formula XXXI can be converted to the compound of formula XXXII by Sandmeyer reaction in one step via preparation of its diazonium salt of the compound of formula XXXI using sodium nitrite and HX and subsequent displacement with a nucleophile for example anhydrous copper bromide, alkali metal iodide such as sodium and potassium iodide and the like. Generally the reaction is carried out at temperatures of from 0° C. to reflux. Any of the conditions conventionally used in Sandmeyer reactions can be utilized to carry out the reaction of step (w).

The compound of formula XXXII can be converted to the compound of formula V by deprotection of the hydroxyl-protecting group. The suitable deprotecting reagents can be described in the Protective Groups in Organic Synthesis by T. Greene.

The product can be isolated and purified by techniques such as extraction, evaporation, chromatography, and recrystallization.

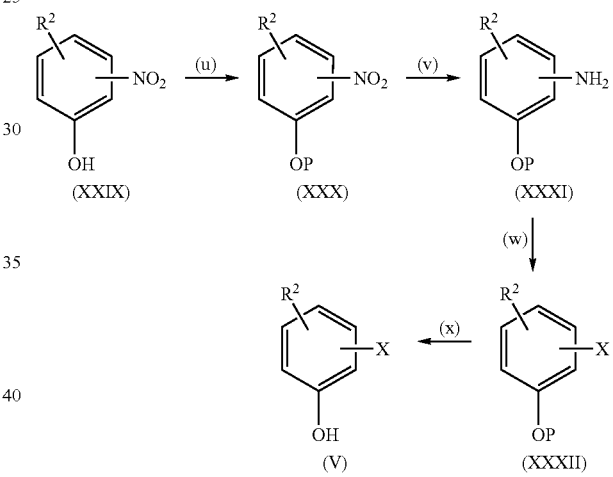

Use in Methods of Treatment

This invention provides a method for treating a mammalian subject with a condition selected from the group consisting of insulin resistance syndrome, diabetes (both primary essential diabetes such as Type I Diabetes or Type II Diabetes and secondary nonessential diabetes) and polycystic ovary syndrome, comprising administering to the subject an amount of a biologically active agent as described herein effective to treat the condition. In accordance with the method of this invention a symptom of diabetes or the chance of developing a symptom of diabetes, such as atherosclerosis, obesity, hypertension, hyperlipidemia, fatty liver disease, nephropathy, neuropathy, retinopathy, foot ulceration and cataracts, each such symptom being associated with diabetes, can be reduced. This invention also provides a method for treating hyperlipidemia comprising administering to the subject an amount of a biologically active agent as described herein effective to treat the condition. Compounds reduce serum triglycerides and free fatty acids in hyperlipidemic animals. This invention also provides a method for treating cachexia comprising administering to the subject an amount of a biologically active agent as described herein effective to treat the cachexia. This invention also provides a method for treating obesity comprising administering to the subject an amount of a biologically active agent as described herein effective to treat the condition. This invention also provides a method for treating a condition selected from atherosclerosis or arteriosclerosis comprising administering to the subject an amount of a biologically active agent as described herein effective to treat the condition. The active agents of this invention are effective to treat hyperlipidemia, fatty liver disease, cachexia, obesity, atherosclerosis or arteriosclerosis whether or not the subject has diabetes or insulin resistance syndrome. The agent can be administered by any conventional route of systemic administration. Preferably the agent is administered orally. Accordingly, it is preferred for the medicament to be formulated for oral administration. Other routes of administration that can be used in accordance with this invention include rectally, parenterally, by injection (e.g. intravenous, subcutaneous, intramuscular or intraperitoneal injection), or nasally.

Further embodiments of each of the uses and methods of treatment of this invention comprise administering any one of the embodiments of the biologically active agents described above. In the interest of avoiding unnecessary redundancy, each such agent and group of agents is not being repeated, but they are incorporated into this description of uses and methods of treatment as if they were repeated.

Many of the diseases or disorders that are addressed by the compounds of the invention fall into two broad categories: Insulin resistance syndromes and consequences of chronic hyperglycemia. Dysregulation of fuel metabolism, especially insulin resistance, which can occur in the absence of diabetes (persistent hyperglycemia) per se, is associated with a variety of symptoms, including hyperlipidemia, atherosclerosis, obesity, essential hypertension, fatty liver disease (NASH; nonalcoholic steatohepatitis), and, especially in the context of cancer or systemic inflammatory disease, cachexia. Cachexia can also occur in the context of Type I Diabetes or late-stage Type II Diabetes. By improving tissue fuel metabolism, active agents of the invention are useful for preventing or ameliorating diseases and symptoms associated with insulin resistance. While a cluster of signs and symptoms associated with insulin resistance may coexist in an individual patient, it many cases only one symptom may dominate, due to individual differences in vulnerability of the many physiological systems affected by insulin resistance. Nonetheless, since insulin resistance is a major contributor to many disease conditions, drugs which address this cellular and molecular defect are useful for prevention or amelioration of virtually any symptom in any organ system that may be due to, or exacerbated by, insulin resistance.

When insulin resistance and concurrent inadequate insulin production by pancreatic islets are sufficiently severe, chronic hyperglycemia occurs, defining the onset of Type II diabetes mellitus (NIDDM). In addition to the metabolic disorders related to insulin resistance indicated above, disease symptoms secondary to hyperglycemia also occur in patients with NIDDM. These include nephropathy, peripheral neuropathy, retinopathy, microvascular disease, ulceration of the extremities, and consequences of nonenzymatic glycosylation of proteins, e.g. damage to collagen and other connective tissues. Attenuation of hyperglycemia reduces the rate of onset and severity of these consequences of diabetes. Because active agents and compositions of the invention help to reduce hyperglycemia in diabetes, they are useful for prevention and amelioration of 14 complications of chronic hyperglycemia.

Both human and non-human mammalian subjects can be treated in accordance with the treatment method of this invention. The optimal dose of a particular active agent of the invention for a particular subject can be determined in the clinical setting by a skilled clinician. In the case of oral administration to a human for treatment of disorders related to insulin resistance, diabetes, hyperlipidemia, fatty liver disease, cachexia or obesity the agent is generally administered in a daily dose of from 1 mg to 400 mg, administered once or twice per day. In the case of oral administration to a mouse the agent is generally administered in a daily dose from 1 to 300 mg of the agent per kilogram of body weight. Active agents of the invention are used as monotherapy in diabetes or insulin resistance syndrome, or in combination with one or more other drugs with utility in these types of diseases, e.g. insulin releasing agents, prandial insulin releasers, biguanides, or insulin itself. Such additional drugs are administered in accord with standard clinical practice. In some cases, agents of the invention will improve the efficacy of other classes of drugs, permitting lower (and therefore less toxic) doses of such agents to be administered to patients with satisfactory therapeutic results. Established safe and effective dose ranges in humans for representative compounds are: metformin 500 to 2550 mg/day; glyburide 1.25 to 20 mg/day; GLUCOVANCE (combined formulation of metformin and glyburide) 1.25 to 20 mg/day glyburide and 250 to 2000 mg/day metformin; atorvastatin 10 to 80 mg/day; lovastatin 10 to 80 mg/day; pravastatin 10 to 40 mg/day; and simvastatin 5-80 mg/day; clofibrate 2000 mg/day; gemfibrozil 1200 to 2400 mg/day, rosiglitazone 4 to 8 mg/day; pioglitazone 15 to 45 mg/day; acarbose 75-300 mg/day; repaglinide 0.5 to 16 mg/day.

Type I Diabetes Mellitus: A patient with Type I diabetes manages their disease primarily by self-administration of one to several doses of insulin per day, with frequent monitoring blood glucose to permit appropriate adjustment of the dose and timing of insulin administration. Chronic hyperglycemia leads to complications such as nephropathy, neuropathy, retinopathy, foot ulceration, and early mortality; hypoglycemia due to excessive insulin dosing can cause cognitive dysfunction or unconsciousness. A patient with Type I diabetes is treated with 1 to 400 mg/day of an active agent of this invention, in tablet or capsule form either as a single or a divided dose. The anticipated effect will be a reduction in the dose or frequency of administration of insulin required to maintain blood glucose in a satisfactory range, and a reduced incidence and severity of hypoglycemic episodes. Clinical outcome is monitored by measurement of blood glucose and glycosylated hemoglobin (an index of adequacy of glycemic control integrated over a period of several months), as well as by reduced incidence and severity of typical complications of diabetes. A biologically active agent of this invention can be administered in conjunction with islet transplantation to help maintain the anti-diabetic efficacy of the islet transplant.

Type II Diabetes Mellitus: A typical patient with Type II diabetes (NIDDM) manages their disease by programs of diet and exercise as well as by taking medications such as metformin, glyburide, repaglinide, rosiglitazone, or acarbose, all of which provide some improvement in glycemic control in some patients, but none of which are free of side effects or eventual treatment failure due to disease progression. Islet failure occurs over time in patients with NIDDM, necessitating insulin injections in a large fraction of patients. It is anticipated that daily treatment with an active agent of the invention (with or without additional classes of antidiabetic medication) will improve glycemic control, reduce the rate of islet failure, and reduce the incidence and severity of typical symptoms of diabetes. In addition, active agents of the invention will reduce elevated serum triglycerides and fatty acids, thereby reducing the risk of cardiovascular disease, a major cause of death of diabetic patients. As is the case for all other therapeutic agents for diabetes, dose optimization is done in individual patients according to need, clinical effect, and susceptibility to side effects.

Hyperlipidemia: Elevated triglyceride and free fatty acid levels in blood affect a substantial fraction of the population and are an important risk factor for atherosclerosis and myocardial infarction. Active agents of the invention are useful for reducing circulating triglycerides and free fatty acids in hyperlipidemic patients. Hyperlipidemic patients often also have elevated blood cholesterol levels, which also increase the risk of cardiovascular disease. Cholesterol-lowering drugs such as HMG-CoA reductase inhibitors ("statins") can be administered to hyperlipidemic patients in addition to agents of the invention, optionally incorporated into the same pharmaceutical composition.

Fatty Liver Disease: A substantial fraction of the population is affected by fatty liver disease, also known as nonalcoholic steatohepatitis (NASH); NASH is often associated with obesity and diabetes. Hepatic steatosis, the presence of droplets of triglycerides with hepatocytes, predisposes the liver to chronic inflammation (detected in biopsy samples as infiltration of inflammatory leukocytes), which can lead to fibrosis and cirrhosis. Fatty liver disease is generally detected by observation of elevated serum levels of liver-specific enzymes such as the transaminases ALT and AST, which serve as indices of hepatocyte injury, as well as by presentation of symptoms which include fatigue and pain in the region of the liver, though definitive diagnosis often requires a biopsy. The anticipated benefit is a reduction in liver inflammation and fat content, resulting in attenuation, halting, or reversal of the progression of NASH toward fibrosis and cirrhosis.

Pharmaceutical Compositions

This invention provides a pharmaceutical composition comprising a biologically active agent as described herein and a pharmaceutically acceptable carrier. Further embodiments of the pharmaceutical composition of this invention comprise any one of the embodiments of the biologically active agents described above. In the interest of avoiding unnecessary redundancy, each such agent and group of agents is not being repeated, but they are incorporated into this description of pharmaceutical compositions as if they were repeated.

Preferably the composition is adapted for oral administration, e.g. in the form of a tablet, coated tablet, dragee, hard or soft gelatin capsule, solution, emulsion or suspension. In general the oral composition will comprise from 1 mg to 400 mg of such agent. It is convenient for the subject to swallow one or two tablets, coated tablets, dragees, or gelatin capsules per day. However the composition can also be adapted for administration by any other conventional means of systemic administration including rectally, e.g. in the form of suppositories, parenterally, e.g. in the form of injection solutions, or nasally.

The biologically active compounds can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semil-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances, particularly antidiabetic or hypolipidemic agents that act through mechanisms other than those underlying the effects of the compounds of the invention. Agents which can advantageously be combined with 28 compounds of the invention in a single formulation include but are not limited to biguanides such as metformin, insulin releasing agents such as the sulfonylurea insulin releaser glyburide and other sulfonylurea insulin releasers, cholesterol-lowering drugs such as the "statin" HMG-CoA reductase inhibitors such as atrovastatin, lovastatin, pravastatin and simvastatin, PPAR-alpha agonists such as clofibrate and gemfibrozil, PPAR-gamma agonists such as thiazolidinediones (e.g. rosiglitazone and pioglitazone, alpha-glucosidase inhibitors such as acarbose (which inhibit starch digestion), and prandial insulin releasers such as repaglinide. The amounts of complementary agents combined with compounds of the invention in single formulations are in accord with the doses used in standard clinical practice. Established safe and effective dose ranges for certain representative compounds are set forth above.

The invention will be better understood by reference to the following examples which illustrate but do not limit the invention described herein.

EXAMPLES

Example A

Improvement of Metabolic Abnormalities in Insulin-Dependent Diabetes

Streptozotocin (STZ) is a toxin that selectively destroys insulin-producing pancreatic beta cells, and is widely used to induce insulin-dependent diabetes in experimental animals.

Female Balb/C mice (8 weeks old; 18-20 grams body weight) are treated with streptozotocin (STZ) (50 mg/kg i.p. on each of five consecutive days). Fourteen days after the last dose of STZ, blood glucose is measured to verify that the animals are diabetic, and the mice are divided into two groups of 5 animals each, one group receiving a compound of the invention (250 mg/kg) daily by oral gavage, and the other receiving vehicle (0.75% hydroxypropylmethylcellulose, a suspending agent, in water). A group of nondiabetic mice from the same cohort that did not receive STZ is also monitored. Blood samples are taken periodically for determination of blood glucose concentrations, and body weights are also recorded.

After several weeks of treatment, blood glucose concentrations in mice treated orally with the compound of the invention and in vehicle-treated control animals are measured. A blood glucose concentration beginning to decrease toward baseline is considered a positive result, whereas blood glucose in the vehicle-treated control animals is expected to continue to rise. Body weights and blood glucose, triglyceride and cholesterol concentrations 14 weeks after the beginning of drug treatment are measured.

Example B

Improved Survival of Mice with Lethal Insulin-Dependent Diabetes

Female Balb/C mice (14 weeks old) are treated with a single dose of streptozotocin (175 mg/kg i.p.) to induce severe insulin-dependent diabetes. Seven days later, mice are divided into three treatment groups: A compound of the invention, pioglitazone, and vehicle. Mice are treated daily via oral gavage, and survival is monitored over time.

Example C

Reduction of Mortality in Severe Insulin-Dependent Diabetes

Female balb/C mice (19 wks of age at start of experiment) are challenged with multiple high doses of STZ (75 mg/kg i.p. on 5 consecutive days). Animals are then divided in two groups (20 mice/group) matched for severity of diabetes. Four days after the last dose of STZ, treatments are initiated. One group receives Vehicle (0.4 ml of 0.75% HPMC, p.o.), and the other group receives a compound of the invention orally (30 mg/kg/day). After three weeks of daily treatment, cumulative mortality in the two groups is recorded.

Example D

Reduction in the Incidence of Spontaneous Diabetes and Mortality in Nod Mice A substantial proportion of NOD ("non-obese diabetic") mice develop insulin-dependent diabetes as a consequence of spontaneous autoimmune destruction of pancreatic islet cells. Two groups of 20 NOD mice (6 weeks old) are treated daily with either oral Vehicle (0.4 ml of 0.75% hydroxypropyl methylcellulose in water; HPMC) or a compound of the invention (200 mg/kg/day) suspended in HPMC. The incidence of mortality due to spontaneous development of severe insulin-dependent diabetes is monitored over a period of seven months.

Example E

Reduction in Hyperglycemia and Hyperlipidemia, and Amelioration of Fatty Liver Disease in Ob/Ob Obese Diabetic Mice Ob/ob mice have a defect in the gene for leptin, a protein involved in appetite regulation and energy metabolism, and are hyperphagic, obese, and insulin resistant. They develop hyperglycemia and fatty liver.

Male lean (ob/+heterozygote) and obese (ob/ob homozygote) C57BL/6 mice approximately 8 weeks of age are obtained from Jackson Labs (Bar Harbor, Me.) and randomly assigned into groups of 5 animals such that body weights and blood glucose concentrations are similar between groups. All animals are maintained under the control of temperature (23 C), relative humidity (50±5%) and light (7:00-19:00), and allowed free access to water and laboratory chow (Formulab Diet 5008, Quality Lab Products, Elkridge, Md.). Blood glucose is routinely determined with glucose test strips and a Glucometer Elite XL device (Bayer Corporation). At selected time points, blood samples (~100 microliters) are obtained with a heparinized capillary tube via the retro-orbital sinus for serum chemistry analysis. Serum chemistry (glucose, triglycerides, cholesterol, BUN, creatinine, AST, ALT, SDH, CPK and free fatty acids) analyses are performed on a Hitachi 717 Analyzer, and plasma insulin and pancreatic insulin are measured by an electrochemiluminescent immunoassay (Origen Analyzer, Igen, Inc., Gaithersburg, Md.).

Groups of ob/ob mice are divided into treatment cohorts as indicated below, and given daily oral doses of a compound of the invention (10, 30, 100, 150 or 300 mg), rosiglitazone (1, 3, 10 or 30 mg), or pioglitazone (30 or 100 mg). The latter two compounds are insulin-sensitizing drugs used in the treatment of human patients with non-insulin dependent diabetes mellitus, and are used as comparators for efficacy and safety of compounds of the invention. The dose ranges of compounds in this experiment is chosen to include both suboptimal and potentially supraoptimal doses.

Ob/ob mice develop chronic inflammatory fatty liver disease and are considered to be an animal model for nonalcoholic steatohepatitis (NASH), a condition which can lead toward progressive cirrhosis and liver dysfunction. In NASH, fat accumulation increases the susceptibility of the liver to inflammatory injury. One characteristic sign of NASH in patients is, in the absence of viral infection or alcoholism, elevated levels in serum of enzymes that are released from damaged hepatocytes, e.g. alanine aminotransferase (ALT), aspartate aminotransferase (AST), and sorbitol dehydrogenase (SDH). These enzymes are elevated in ob/ob mice as a consequence of fatty liver and secondary inflammation.

Example F

Acute Hypoglycemic Effects of Compounds of the Invention in Diabetic Mice: Experiment 1.

Compounds of the invention display acute antihyperglycemic activity in animals with non insulin-dependent diabetes.

Male ob/ob diabetic mice are randomized into groups of five animals each. Body weights are about 50-55 g and blood glucose is approximately 300 mg/dL in the fed state. A single oral dose of a test substance suspended in 0.5% carboxymethylcellulose vehicle is administered by gavage. Blood glucose is measured in blood droplets obtained by nicking a tail vein with a razor using glucometer test strips and a Glucometer Elite XL device (Bayer) at 0, 0.5, 2, 4, 6 and 18 hours after the initial dosing. A 10% reduction in blood glucose versus oral vehicle is considered a positive screening result. Blood glucose reductions are generally expected to be maximal at 6 hours after drug administration.

Example G

Acute Hypoglycemic Effects of Compounds of the Invention in Diabetic Mice: Expt 2

Compounds of the invention display acute antihyperglycemic activity in animals with noninsulin-dependent diabetes.

Male ob/ob mice (50-55 grams; blood glucose ~300 mg/dL) are divided into groups of five animals each, and given a single oral dose of test drug (250 mg/kg) suspended in 0.5% carboxymethylcellulose vehicle; a control group received oral vehicle alone. Six hours after oral administration of test drugs or vehicle (control), blood samples are obtained from a tail vein and glucose content is determined with a glucometer.

Example H

Antidiabetic Effects of Compounds of the Invention in Db/Db Mice

Db/db mice have a defect in leptin signaling, leading to hyperphagia, obesity and diabetes. Moreover, unlike ob/ob mice which have relatively robust islets, their insulin-producing pancreatic islet cells undergo failure during chronic hyperglycemia, so that they transition from hyperinsulinemia (associated with peripheral insulin resistance) to hypoinsulinemic diabetes.

Male db/db mice are given daily oral treatments with vehicle (0.75% hydroxypropylmethylcellulose), a compound of the invention (150 mg/kg), or pioglitazone (100 mg/kg). Blood samples are obtained via the retro-orbital sinus for serum chemistry analysis, or via the tail vein for glucose measurement with a test strip and glucometer. The dose of pioglitazone used in this experiment was reported in the literature to be a maximally-effective dose for treatment of db/db mice (Shimaya et al. (2000), *Metabolism* 49:411-7).

In a second experiment in db/db mice, antidiabetic activity of a compound of the invention (150 mg/kg) is compared with that of rosiglitazone (20 mg/kg). After 8 weeks of treatment, blood glucose and triglycerides are measured. significantly lower in animals treated with either Compound BI or rosiglitazone, compared to vehicle-treated controls. The rosiglitazone dose used in this study was reported in published literature as the optimum dose for late stage db/db mice (Lenhard et al., (1999) *Diabetologia* 42:545-54). Groups consist of 6-8 mice each.

Example I

Antidiabetic Effects of Compounds of the Invention in Db/Db Mice db/db mice have a defect in leptin signaling, leading to hyperphagia, obesity and diabetes. Moreover, unlike ob/ob mice on a C57BL/6J background, db/db mice on a C57BL/KS background undergo failure of their insulin-producing pancreatic islet β cells, resulting in progression from hyperinsulinemia (associated with peripheral insulin resistance) to hypoinsulinemic diabetes.

Male obese (db/db homozygote) C57BL/Ksola mice approximately 8 weeks of age, are obtained from Jackson Labs (Bar Harbor, Me.) and randomly assigned into groups of 5-7 animals such that the body weights (50-55 g) and serum glucose levels ($\geq$300 mg/dl in fed state) are similar between groups; male lean (db/+heterozygote) mice serve as cohort controls. A minimum of 7 days is allowed for adaptation after arrival. All animals are maintained under controlled temperature (23° C.), relative humidity (50±5%) and light (7:00-19:00), and allowed free access to standard chow (Formulab Diet 5008, Quality Lab Products, Elkridge, Md.) and water.

Treatment cohorts are given daily oral doses of (1% hydroxypropylmethylcellulose) or a compound of the invention (100 mg/kg) for 2 weeks. At the end of the treatment period 100 µl of venous blood is withdrawn in a heparinized capillary tube from the retro -orbital sinus of db/db mice for serum chemistry analysis.

Effects of compounds of the invention on nonfasting blood glucose and on serum triglycerides and free fatty acids are measured.

Example J

Attenuation of Cataractogenesis of Compounds of the Invention in Zucker Diabetic Fatty (ZDF) Rats Cataracts are one of the leading causes of progressive vision decline and blindness associated with ageing and diabetes, and the Zucker diabetic fatty (ZDF) model has many similarities with human cataractogenesis, including biochemical changes and oxidative stress in the lens. These rats, however, undergo cataractogenesis typically between 14-16 weeks of age.

Male ZDF rats and their aged-match Zucker lean (ZL) counterparts (fa/+ or +/+) are obtained from Genetic Models, Inc. (Indianapolis, Ind.) aged 12 weeks and acclimatized for 1 week prior to study. All animals are maintained under controlled temperature (23° C.), relative humidity (50±5%) and light (7:00-19:00), and allowed free access to standard chow (Formulab Diet 5008, Quality Lab Products, Elkridge, Md.) and tap water ad libitum. Treatment cohorts are given a daily oral dose of vehicle and 100 mg/kg of a compound of the invention for 10 weeks. Body weights and blood glucose are routinely determined (once a week, usually around 10:00 A.M.) from tail bleeds with glucose test strips and a Glucometer Elite XL device (Bayer Corporation). At the end of the treatment period 100 µl of venous blood is collected (usually 10:00 A.M.) in a heparinized tube from the tail vein for serum chemistry analysis (Anilytics, Inc., Gaithersburg, Md.). Serum chemistry (glucose (GL), triglycerides (TG), aspartate aminotransferase (AST), alanine aminotransferase (ALT), sorbitol dehydrogenase (SDH), and free fatty acids (FFA)) analyses are performed on a Hitachi 717 Analyzer (Anilytics, Inc., Gaithersburg, Md.). Plasma insulin is measured by an electrochemiluminescent immunoassay, ECL (Origen Analyzer, Igen, Inc., Gaithersburg, Md.). The animals are sacrificed and tissues and/or organs (lens and liver) are extirpated, weighed (wet weight) and processed for biochemical analyses. Malondialdehyde (MDA), a major product of lipid peroxidation is assayed in lenses according to Ohkawa et al (1979), Analytical Biochem 95, 351-358).

Example K

Lowering of Circulating Triglycerides, Free Fatty Acids, Insulin and Leptin in High Fat-Fed C57B1/6J Mice The high fat-fed mouse is a model for the hypertriglyceridemia and high circulating fatty acid levels, and the insulin and leptin resistance that are found in people at risk for and with obesity, diabetes, cardiovascular disease and other disorders. Male C57B1/6J mice, approximately 8 weeks of age, are randomly assigned into groups of 6 animals. They are maintained under controlled temperature (23° C.), relative humidity (50±5%) and light (7:00-19:00), and allowed free access to food and water ad libitum. Mice are fed a high-fat diet (diet number D112451, containing 45% of calories as fat (Research Diets, New Brunswick, N.J.)) for 6 weeks. After the 6 weeks, groups of mice received either vehicle (hydroxymethylcellulose), a compound of the invention (10 mg/kg, 30 mg/kg, or 100 mg/kg) Wy14,643 (10 mg/kg, 30 mg/kg, or 100 mg/kg) or rosiglitazone (1 mg/kg, 3 mg/kg, 10 mg/kg, or 100 mg/kg) by oral gavage for an additional 4 weeks while continuing on the high-fat diet. Plasma chemistries (Anilytics, Inc., Gaithersburg, Md.) are assayed after 2 weeks of drug treatments. Plasma serum insulin and leptin are measured by an electrochemiluminescent immunoassay (Origen Analyzer, Igen, Inc., Gaithersburg, Md.) after 4 weeks of drug treatments.

Example L

Lowering of Circulating Triglycerides, Free Fatty Acids, Insulin and Leptin in High Fat-Fed Sprague Dawley Rats The high fat-fed rat is a model for insulin and leptin resistance. Sprague-Dawley rats have an intact leptin system and respond to a high fat diet with hyperinsulinemia due to a downregulation of the normal insulin response in peripheral tissues such as liver, adipose tissue and muscle Male Sprague-Dawley rats, approximately 17 weeks of age, are obtained from Jackson Labs (Bar Harbor, Me.) and randomly assigned into groups of 5-7 animals; the body weights are similar between groups. All animals are maintained in a temperature-controlled (25° C.) facility with a strict 12 h light/dark cycle and are given free access to water and food. Rats are fed a high-fat diet (diet number D12451 (containing 45% of calories as fat), Research Diets, New Brunswick, N.J.) for one month prior to drug treatment.

Groups of 6 Sprague-Dawley rats are treated with a single daily dose of vehicle (hydroxymethylcellulose), a compound of the invention (10, 30 and 100 mg/kg), or rosiglitazone (3 mg/kg) for 6 weeks while maintaining the high-fat diet. Blood samples (~100 μl) are obtained via the tail vein for serum chemistry analysis.

What is claimed is:

1. A compound of the formula:

$$A(CH_2)_t(N)_q(CH_2)_n-O-\text{[aryl]}-OH, F, F, R^1, R^2 \quad I$$

wherein
n is 1 or 2;
q is 0 or 1;
t is 0 or 1;
$R^1$ is alkyl having from 1 to 3 carbon atoms;
$R^2$ is hydrogen, halo, alkyl having from 1 to 3 carbon atoms, or alkoxy having from 1 to 3 carbon atoms;
A is phenyl, unsubstituted or substituted by 1 or 2 groups selected from: halo, alkyl having 1 or 2 carbon atoms, perfluoromethyl, hydroxy, alkoxy having 1 or 2 carbon atoms, and perfluoromethoxy; or
cycloalkyl having from 3 to 6 ring carbon atoms wherein the cycloalkyl is unsubstituted or one or two ring carbons are independently mono-substituted by methyl or ethyl; or
a 5 or 6 membered heteroaromatic ring having 1 or 2 ring heteroatoms selected from N, S and O and the heteroaromatic ring is covalently bound to the remainder of the compound of formula I by a ring carbon;
or a pharmaceutically acceptable salt of the compound.

2. The compound or salt of claim 1, wherein n is 1; q is 0; t is 0; $R^2$ is hydrogen; and
A is phenyl, unsubstituted or substituted by 1 or 2 groups selected from: halo, alkyl having 1 or 2 carbon atoms, perfluoromethyl, hydroxy, alkoxy having 1 or 2 carbon atoms, and perfluoromethoxy.

3. The compound or salt of claim 2, wherein A is 2,6-dimethylphenyl.

4. The compound or salt of claim 3, wherein the compound is 2,6-Difluoro-4-(3-(2,6-dimethylbenzyloxy)phenyl)phenol.

5. A pharmaceutical composition adapted for oral administration, comprising a pharmaceutically acceptable carrier and from one milligram to four hundred milligrams of a biologically active agent, wherein the agent is a compound of the formula:

$$A(CH_2)_t(N)_q(CH_2)_n-O-\text{[aryl]}-OH, F, F, R^1, R^2 \quad I$$

wherein
n is 1 or 2;
q is 0 or 1;
t is 0 or 1;
$R^1$ is alkyl having from 1 to 3 carbon atoms;
$R^2$ is hydrogen, halo, alkyl having from 1 to 3 carbon atoms, or alkoxy having from 1 to 3 carbon atoms;
A is phenyl, unsubstituted or substituted by 1 or 2 groups selected from: halo, alkyl having 1 or 2 carbon atoms, perfluoromethyl, hydroxy, alkoxy having 1 or 2 carbon atoms, and perfluoromethoxy; or
cycloalkyl having from 3 to 6 ring carbon atoms wherein the cycloalkyl is unsubstituted or one or two ring carbons are independently mono-substituted by methyl or ethyl; or
a 5 or 6 membered heteroaromatic ring having 1 or 2 ring heteroatoms selected from N, S and O and the heteroaromatic ring is covalently bound to the remainder of the compound of formula I by a ring carbon;
or a pharmaceutically acceptable salt of the compound.

6. The pharmaceutical composition of claim 5, wherein n is 1; q is 0; t is 0;
$R^2$ is hydrogen; and
A is phenyl, unsubstituted or substituted by 1 or 2 groups selected from: halo, alkyl having 1 or 2 carbon atoms, perfluoromethyl, hydroxy, alkoxy having 1 or 2 carbon atoms, and perfluoromethoxy.

7. The pharmaceutical composition of claim 6, wherein A is 2,6-dimethylphenyl.

8. The pharmaceutical composition t of claim 7, wherein the compound is 2,6-Difluoro-4-(3-(2,6-dimethylbenzyloxy)phenyl)phenol.

9. The pharmaceutical composition of claim 8 in oral dosage form.

10. The pharmaceutical composition of claim 5 in oral dosage form.

* * * * *